United States Patent [19]
Amarilli et al.

[11] Patent Number: 6,005,152
[45] Date of Patent: Dec. 21, 1999

[54] PROCESS FOR THE PREPARATION OF MONOALKYLATED AROMATIC COMPOUNDS

[75] Inventors: Stefano Amarilli, Maggiora; Luciano Carluccio, Milan; Carlo Perego, Carnate; Giuseppe Bellussi, Piacenza, all of Italy

[73] Assignees: Enichem S.p.A.; EniTechnologie S.p.A., both of San Donato Milanese, Italy

[21] Appl. No.: 09/285,752

[22] Filed: Apr. 5, 1999

[30] Foreign Application Priority Data

Apr. 7, 1998 [IT] Italy ................................ M198A0735

[51] Int. Cl.$^6$ ................................ C07C 1/00; C07C 2/68; C07C 2/64; C07C 5/22
[52] U.S. Cl. ........................... 585/467; 585/475; 585/423; 585/449
[58] Field of Search ...................................... 585/467, 475, 585/323, 449; 502/64

[56] References Cited

U.S. PATENT DOCUMENTS 5,910,299  6/1999  Carluccio et al. ...................... 423/706

FOREIGN PATENT DOCUMENTS 0 796 821  9/1997  European Pat. Off. .

*Primary Examiner*—Walter D. Griffin
*Assistant Examiner*—Thuan D. Dang
*Attorney, Agent, or Firm*—Oblon, Spivak, McClelland, Maier & Neustadt, P.C.

[57] ABSTRACT

A process is described for preparing monoalkylated aromatic compounds which comprises subjecting an aromatic hydrocarbon to alkylation with an olefin containing from 2 to 4 carbon atoms, or to transalkylation with a polyalkylaromatic hydrocarbon, in the presence of ERS-10 zeolite.

37 Claims, No Drawings

PROCESS FOR THE PREPARATION OF MONOALKYLATED AROMATIC COMPOUNDS

A process is described for preparing monoalkylated aromatic compounds which comprises subjecting an aromatic hydrocarbon to alkylation with an olefin containing from 2 to 4 carbon atoms, or to transalkylation with a polyalkylaromatic hydrocarbon, in the presence of ERS-10 zeolite.

Former processes, still widely used in the petro-chemical industry, for the production of alkylaromatics, and in particular cumene and ethylbenzene, comprise the use of a catalyst based on phosphoric acid and infusorial earth, in a fixed bed, for cumene and $AlCl_3$, in slurry, for ethylbenzene and cumene. With these processes however there are problems relating to environmental impact and safety; in fact, the use of these catalysts is particularly problematical owing to corrosion, the by-production of toxic organic products and the disposal of the exhausted catalysts. The possibility of substituting these catalysts with non-polluting, non-corrosive and regenerable materials such as for example zeolitic catalysts, has been known for some time. The use of X and Y zeolites for the preparation of cumene was described for the first time in 1965 (Minachev, Kr. M., Isakov, Ya. I., Garanin, V. I., Piguzova, L. I. Bogomov, V. I., and Vitukina, A. S., Neftekhimiya 5 (1965) 676). Subsequently Venuto et al. (Venuto, P. B., Hamilton, L. A., Landis, P. S., and Wise, J. J., J. Catal. 5, (1966) 81) described the alkylation of benzene with light olefins, such as propylene and ethylene, catalyzed by zeolites with a faujasitic structure (X and Y), and therefore with wide pores.

These zeolites can be stabilized by exchange with rare earth. U.S. Pat. No. 3,251,897 describes the alkylation of aromatics in liquid phase, catalyzed by porous crystalline alumino-silicates, among which X, Y and mordenite.

U.S. Pat. No. 4,292,458 describes the use of ZSM-5 type zeolites, in particular a boralite with an ZSM-5 type structure capable of catalyzing the alkylation of benzene with propylene. This type of zeolitic system however, perhaps owing to the channels which are too small, only allows the production of cumene with rather low selectivities. It can generally be said therefore that zeolites are active in the alkylation of aromatics with olefins, but have different behaviour with respect to the selectivity. The alkylation reaction is in fact accompanied by succesive secondary reactions, such as polyalkylation, and parallel reactions such as the oligomerization of olefins. The oligomers may then in turn alkylate the aromatic giving heavy alkylated products or undergo cracking to give light olefins, different from the main reagent, thus producing, by successive alkylation, other alkylated by-products.

Preparations of monoalkylated hydrocarbons by the transalkylation of polyalkylated aromatic hydrocarbons in which zeolites with small, medium and large pores are used, are described for example in U.S. Pat. No. 3,385,906, U.S. Pat. No. 4,169,111 and EP 308097.

In particular the transalkylation reaction of polyalkylated aromatic hydrocarbons can be appropriately carried out subsequently to the alkylation step, by operating on the polyalkylated products recovered downstream of the alkylation. The use of zeolitic catalysts for preparing monoalkylated aromatic hydrocarbons by the transalkylation of polyalkylated products in a step subsequent to the alkylation step is described in U.S. Pat. No. 3,385,906, U.S. Pat. No. 4,774,377, U.S. 4,168,111 and EP 308097, where alkylation and transalkylation processes are combined to obtain better yields to monoalkylated aromatics.

EP 432,814, EP 439,632, EP 629599 and EP 687500 describe the production of monoalkylated aromatic hydrocarbons from aromatic hydrocarbons by alkylation, transalkylation and a combined alkylation and transalkylation process, catalyzed by beta zeolite.

A process has now been found for preparing monoalkylated aromatic compounds which comprises subjecting an aromatic hydrocarbon to alkylation with an olefin containing from 2 to 4 carbon atoms, or to transalkylation tion with a polyalkylaromatic hydrocarbon, in the presence of a catalyst containing ERS-10 zeolite.

Better results are obtained with the present invention in terms of selectivity to monoalkylated product; in the alkylation process, in particular, there is a low formation of heavy products (dialkylated products) and n-propylbenzene.

ERS-10 zeolite is a porous crystalline material described in EP 796821, having a molar composition of oxides in its calcined and anhydrous form, corresponding to the following formula:

$$mM_{2/n}O.zX_2O_3.YO_2$$

wherein m is a number between 0.01 and 10, M is $H^+$ and/or a cation of an alkaline or earth-alkaline metal with a valence n, z is a number between 0 and 0.02, X represents one or more elements selected from aluminum, iron, gallium, boron, vanadium, arsenic, antimonium, chromium and manganese and Y represents one or more elements selected from silicon, germanium, titanium, zirconium, characterized by the following X-ray diffraction spectrum from powders (recorded by means of a vertical goniometer equipped with an electronic impulse-count system and using CuKα (λ=1.54178 A) containing the main reflections indicated in Table A:

TABLE A

| d(Å) | $I/I_0 \cdot 100$ |
|---|---|
| 11.0 + 0.1 | vs |
| 6.80 + 0.08 | w |
| 5.79 + 0.06 | w |
| 4.59 + 0.05 | m |
| 4.29 + 0.05 | vs |
| 3.96 + 0.04 | m |
| 3.69 + 0.03 | w |
| 3.41 + 0.03 | w |
| 3.33 + 0.03 | w |
| 3.26 + 0.02 | m |
| 3.07 + 0.02 | w |
| 2.68 + 0.01 | w |
| 2.57 + 0.01 | w |
| 2.51 + 0.01 | w |
| 2.38 + 0.01 | w |
| 2.31 + 0.01 | w |
| 2.28 + 0.01 | w |
| 2.11 + 0.01 | w |
| 2.03 + 0.01 | w |
| 1.94 + 0.01 | w | wherein d indicates the interplane distance, $I/I_0.100$ represents the relative intensity calculated by measuring the height of the peaks and percentually relating it to the height of the most intense peak, the symbol vs indicates a very strong intensity (60–100), s a strong intensity (40–60), m a medium intensity (20–40) and w a weak intensity (0–20).

M is preferably selected from sodium, potassium, hydrogen or their mixtures. According to a particularly preferred aspect of the present invention, the ERS-10 zeolite is in acid form i.e. in the form in which the cationic sites M of the zeolite are prevalently occupied by hydrogen ions. It is especially preferable for at least 80% of the cationic sites to be occupied by hydrogen ions. X is preferably aluminum and Y is preferably silicon. The zeolite can be used as such or extruded with suitable binding inorganic oxides to form cylindrical or spherical pellets, or pellets with other forms commonly used. The ligands for example can be aluminas, silicons, silicoaluminas, clays. Alumina is preferably used. The end-catalyst contains from 10 to 90%, preferably from 20 to 80% by weight of ERS-10 zeolite.

The aromatic hydrocarbons which can be alkylated or transalkylated according to the present invention are benzene, toluene, xylene and their mixtures. The aromatic hydrocarbon is preferably benzene.

The olefins which are used for the alkylation of aromatic hydrocarbons according to the present invention are olefins containing from 2 to 4 carbon atoms, preferably ethylene or propylene. The olefins are pure or mixed with $C_2$–$C_4$ paraffins, but are preferably without dienes, acetylenes, sulfurated compounds or compounds containing nitrogen, which could deactivate the catalyst.

The polyalkylated aromatic hydrocarbons which are used for transalkylation are those containing two or more alkyl groups each of which can have from 2 to 4 carbon atoms. They are preferably dialkylbenzenes such as diethylbenzenes or diisopropylbenzenes. Reaction products which are preferably prepared with the process of the present invention are ethylbenzene obtained by the reaction of benzene with ethylene or polyethylbenzenes, preferably diethylbenzenes, and cumene by the reaction of benzene with propylene or with polyisopropylbenzenes, preferably diisopropylbenzenes.

The alkylation reaction can be industrially effected in continuous, semicontinuous or batch, and in gaseous phase, liquid phase or mixed phase; in order to keep the temperature within a preferred range and reduce the by-production of aromatic polyalkylated products, the catalyst can be arranged in various layers in the reactor. A quench is effected between one layer and another with inert solvents and/or part of the aromatic and/or part of the olefin.

Under suitable conditions, high aromatic/olefin ratios can be obtained on the single layer, without increasing the overall ratio, to the evident advantage of the subsequent separation and recycling of the aromatic. The temperature control can be carried out either by the quenching of reagents and/or inert products, or by intercooling between the layers, for example by the insertion of coolants. The alkylation reaction can be appropriately carried out in two or more reactors in series, intercooled to control the temperature. The feeding of the olefins can be suitably distributed among the various reactors and reactor layers, optionally diluting the olefin itself with an aromatic or inert product to favour the temperature control. The feeding of the olefin is in such a quantity as to obtain a molar ratio of Aromatic to olefin ranging from 1 to 20, preferably between 2 and 8.

The reaction temperature ranges from 100° C. to 300° C., preferably between 120° C. and 230° C.; the pressure ranges from 10 atms to 50 atms, preferably from 20 atms to 45 atms; the WHSV space velocity ranges from 0.1 to 200 hours$^{-1}$, preferably between 1 and 10 hours$^{-1}$. A combination of temperature and pressure conditions is preferably selected so as to guarantee that the alkylation reaction takes place at least partially in liquid phase, and even more preferably substantially in liquid phase.

The transalkylation reaction is carried out at a temperature ranging from 100 to 350° C., at a pressure ranging from 10 to 50 atms and a WHSV ranging from 0.1 to 200 hours$^{-1}$. The temperature is preferably between 150 and 300° C., the pressure between 20 and 45 atms and the WHSV between 0.1 and 10 hours$^{-1}$. The transalkylation reaction is preferably carried out under such conditions as to take place at least partially in liquid phase, even more preferably under such conditions as to take place substantially in liquid phase.

The molar ratio between aromatic hydrocarbon and polyalkylaromatic hydrocarbon can vary from 1 to 30, preferably from 1 to 10.

According to a preferred aspect, in order to maximize the production of monoalkylated product in the reaction of aromatics with light olefins, and in particular benzene with ethylene to give ethylbenzene and benzene with propylene to give cumene, the transalkylation activity of the ERS-10 zeolite can be effected in the same reactor in which the alkylation process takes place, where, with a sufficient residence time, the quantity of polyalkylated by-products can be reduced with respect to the monoalkylated product.

According to another aspect of the present invention, to obtain better yields to monoalkylated product, the product obtained in alkylation can be separated into (a) a fraction of aromatic hydrocarbon, (b) a fraction of monoalkylated aromatic and (c) a fraction of polyalkylated aromatics and this latter fraction is refed to the alkylation reactor where it undergoes the transalkylation reaction to give the monoalkylated product. According to a preferred aspect of the present invention, the fraction of polyalkylated aromatics (c) is subjected to transalkylation in a specific reactor, where it is put in contact with a feeding of aromatic hydrocarbon, in the presence of the catalyst containing ERS-10 zeolite.

For example the "cumene bottoms" fraction produced in the alkylation process to give cumene can be used as polyalkylated aromatic hydrocarbon prevalently consisting of diisopropylbenzenes.

A further aspect of the present invention therefore relates to a process for the preparation of monoalkylated aromatic hydrocarbons which comprises:

1) putting an aromatic hydrocarbon in contact with a $C_2$–$C_4$ olefin, under alkylation conditions, in the presence of a catalyst containing ERS-10 zeolite, 2) separating the product obtained into (a) a fraction containing an aromatic hydrocarbon, (b) a fraction containing a monoalkylated aromatic hydrocarbon and (c) a fraction containing polyalkylated aromatic hydrocarbons, 3) putting the fraction (c) containing polyalkylated aromatic hydrocarbons in contact with an aromatic hydrocarbon, under transalkylation conditions, in the presence of ERS-10 zeolite.

Steps 1) and 3) are preferably carried out under partially liquid phase conditions, even more preferably under substantially liquid phase conditions.

EXAMPLE 1 (preparation of ERS-10 zeolite)

10.4 g of tetraethylortho silicate are added, under stirring, to a solution consisting of 45 g of demineralized water, 0.204 g of aluminum isopropylate, 0.19 g of sodium hydroxide and 1.71 g of 6-azoniaspiro-(5,5)-undecane hydroxide (Q). These operations are carried out at room temperature. When the hydrolysis is complete, an opalescent solution is obtained, having the following composition expressed as molar ratios:

$SiO_2/Al_2O_3=100/1$ $Na^+/SiO_2=0.095/1$ $Q/SiO_2=0.2/1$ $H_2O/SiO_2=50/1$ $OH^-/SiO_2=0.295$.

The solution is then charged into a steel autoclave, situated in an oven and maintained at 170° C., under autogenous pressure, for 14 days. After cooling to room temperature the crystalline product is separated from the mother liquor by filtration, washed with demineralized water and dried in an oven at 120° C. for 2 hours.

The composition of the crystalline material, determined by elemental chemical analysis, is the following:

$67\ SiO_2:1\ Al_2O_3:0.5\ Q_2O:0.3\ Na_2O:7\ H_2O$

The material obtained is a crystalline aluminosilicate having an X-ray diffraction pattern (effected with an vertical goniometer equipped with an electronic impulse-count system using radiation CuKα λ=1.544178 Å) as described in EP 796821, example 1, table 3. The sample is then calcined at 550° C. for 5 hours in a stream of air. Chemical analysis shows the following composition:

$67\ SiO_2:1\ Al_2O_3:0.3\ Na_2O$

The X-ray diffraction spectrum from powders relating to this sample in acid form is that indicated in EP 796821, example 1, table 4.

The calcined product is subsequently subjected to exchange process in acid form by repeated treatment with a solution of ammonium acetate at 80° C., washing with demineralized water and calcination at 550° C. for 5 hours. The sample thus obtained has a residual Na content of less than 100 ppm.

EXAMPLE 2 (alkylation test:synthesis of cumene)

The catalyst in the form of ERS-10 powder obtained in example 1, is made into tablets, sieved into particles having dimensions of 20–40 mesh and tested in an alkylation process of benzene with propylene to give cumene. 3.0 g of this catalyst are charged into a fixed-bed reactor having a diameter of 1.2 cm and equipped with an internal thermometer container into which the thermocouple for the temperature control is inserted. The reactor is immersed in a heated oil bath to obtain better temperature control. The catalyst is first activated in nitrogen at 180° C. to eliminate any residual traces of humidity present therein. The conditions adopted for the alkylation test are:

molar ratio benzene/propylene=7/1
temperature=150° C.
pressure=38 bars
WHSV=1 hours$^{-1}$ The products are analyzed using a gas chromatograph (Hewlett-Packard 5890 equipped with a FID analyzer) having a PONA capillary column (50 m×0.21 mm×0.5 μm).

The following table 1 indicates the results of the test:

| | |
|---|---|
| time on stream (hours) | 22.5 |
| propylene conversion (%) | 99.3 |
| distribution of normalized products with respect to benzene (% weight) | |
| oligomers | 0.25 |
| cumene | 92.64 |
| n-propylbenzene (ppm/cumene) | 158 |
| diisopropylbenzenes (DIPBs) | 5.88 |
| others | 0.92 |
| selectivity (%) | |
| $(C_9/C_6)$ | 94.82 |
| $(C_9/C_3)$ | 89.52 |
| $(IPBS/C_3)$ | 97.93 | wherein:

$(C_9/C_6)$=selectivity to cumene referring to benzene $(C_9/C_3)$=selectivity to cumene referring to propylene $(IPBs/C_3)$=selectivity to isopropylbenzenes (IPBS) (cumene, diisopropylbenzenes) referring to propylene.

EXAMPLE 3 (alkylation test:synthesis of cumene)

Example 2 is repeated under the following conditions:

molar ratio benzene/propylene 7/1
temperature=170° C.
pressure=38 bars
WHSV=1 hour$^{-1}$ Table 2 below indicates the results of the test:

| | |
|---|---|
| time on stream (hours) | 22.5 |
| propylene conversion (%) | 99.5 |
| distribution of normalized products with respect to benzene (% weight) | |
| oligomers | 0.23 |
| cumene | 88.34 |
| n-propylbenzene (ppm/cumene) | 265 |
| diisopropylbenzenes (DIPBs) | 10.45 |
| others | 0.77 |
| selectivity (%) | |
| $(C_9/C_6)$ | 91.37 |
| $(C_9/C_3)$ | 83.71 |
| $(IPBs/C_3)$ | 98.68 |

EXAMPLE 4

Example 2 is repeated under the following conditions:

molar ratio benzene/propylene=7/1
temperature=185° C.
pressure=38 bars
WHSV=1 hour$^{-1}$ Table 3 below indicates the results of the test:

| | |
|---|---|
| time on stream (hours) | 87.5 |
| propylene conversion (%) | 99.5 |
| distribution of normalized products with respect to benzene (% weight) | |
| oligomers | 0.21 |
| cumene | 86.61 |
| n-propylbenzene(ppm/cumene) | 360 |
| diisopropylbenzenes (DIPBs) | 12.3 |
| others | 0.68 |
| selectivity (%) | |
| $(C_9/C_6)$ | 89.98 |
| $(C_9/C_3)$ | 81.43 |
| $(IPBs/C_3)$ | 98.56 |

EXAMPLE 5 (comparative)

Example 2 is repeated using as catalyst a USY zeolite (330 HUA of Tosoh Corporation) under the following conditions:

catalyst charged=3.0 g
molar ratio benzene/propylene=7/1
temperature=150° C.
pressure=38 bars
WHSV=1 hour$^{-1}$
Table 4 below indicates the results of the test:

| | |
|---|---|
| propylene conversion (%) | 98.1 |
| distribution of normalized products with respect to benzene (% weight) | |
| oligomers | 0.33 |
| cumene | 73.05 |
| n-propylbenzene (ppm/cumene) | 170 |
| diisopropylbenzenes (DIPBs) | 21.88 |
| others | 4.51 |
| selectivity (%) | |
| ($C_9/C_6$) | 79.36 |
| ($C_9/C_3$) | 63.69 |
| ($IPBs/C_3$) | 91.93 |

Comparing these results to those obtained, under the same operating conditions, in example 2, it can be observed that the ERS-10 zeolite has a much higher selectivity to cumene than the Y zeolite, with respect to both benzene and propylene. It should also be noted that in both example 2 and comparative example 5 the propylene conversion is total and as far as the production of isopropylbenzenes (IPBs) is concerned, the values obtained with the ERS-10 zeolite are much higher than those obtained with the Y zeolite.

EXAMPLE 6 (comparative)

Example 2 is repeated using as catalyst a CBV40 mordenite (PQ Corporation) under the following conditions:
catalyst charged=3.0 g
molar ratio benzene/propylene=7/1
temperature=150° C.
pressure=38 bars
WHSV=1 hour$^{-1}$
Table 5 below indicates the results of the test:

| | |
|---|---|
| Table 5 below indicates the results of the test: | |
| propylene conversion (%) | 99.8 |
| distribution of normalized products with respect to benzene (% weight) | |
| oligomers | 0.31 |
| cumene | 89.1 |
| n-propylbenzene (ppm/cumene) | 163 |
| diisopropylbenzenes (DIPBs) | 10.58 |
| others | 0.33 |
| selectivity (%) | |
| ($C_9/C_6$) | 91.85 |
| ($C_9/C_3$) | 84.25 |
| ($IPBs/C_3$) | 99.05 |

Comparing these results to those obtained, under the same operating conditions, in example 2, it can be observed that the ERS-10 zeolite has a much higher selectivity to cumene than mordenite, with respect to both benzene and propylene. Also in this case, it should be noted that in both example 2 and comparative example 6 the propylene conversion is total and as far as the production of isopropylbenzenes (IPBs) is concerned, the values obtained with ERS-10 zeolite are much higher than those obtained with mordenite.

It can therefore be asserted in general that ERS-10 zeolite gives rise to a higher production of cumene and a lower formation of by-products such as diiso-propylbenzenes, oligomers and n-propylbenzene.

EXAMPLE 7 —(transalkylation catalytic test)

A transalkylation test is carried out using the ERS-10 catalyst prepared as described in example 1, transformed into pellets having dimensions of 20–40 mesh. The test is effected in a fixed-bed plant in continuous where 2.0 g of catalyst are charged. The liquid feeding consists of a mixture of benzene (80% by weight) and 1,3-diisopropylbenzene (20% by weight). The reaction conditions are the following:
temperature=200, 220 and 2400C
pressure=50 bars
WHSV=5 hours$^{-1}$
The results of the test are indicated in Table 1.

TABLE 1

| Temperature (° C.) | 200 | 220 | 240 |
|---|---|---|---|
| Time on stream (hours) | 4.5–6 | 28.5–30 | 52.5.54 |
| Weight % composition: | | | |
| Benzene | 79.13 | 76.28 | 74.48 |
| $C_6$–$C_9$ Oligomers | 0.01 | 0.04 | 0.09 |
| Cumene | 4.21 | 13.04 | 19.01 |
| n-Propylbenzene | 0.0038 | 0.0650 | 0.3355 |
| 1,2-diisopropylbenzene | 0.06 | 0.06 | 0.04 |
| 1,3-diisopropylbenzene | 13.63 | 7.50 | 3.86 |
| 1,4-diisopropylbenzene | 2.85 | 2.73 | 1.69 |
| $C_6$-Phenyl | 0.02 | 0.08 | 0.15 |
| $C_9$-Phenyl | 0.02 | 0.05 | 0.10 |
| Cumene/diisopropylbenzenes | 0.25 | 1.27 | 3.40 |

We claim:

1. A process for alkylation of aromatic hydrocarons which comprises putting the aromatic hydrocarbon in contact with an olefin containing from 2 to 4 carbon atoms in the presence of a catalyst comprising ERS-10 zeolite.

2. The process according to claim 1 carried out at a temperature ranging from 100 to 300° C., at a pressure ranging from 10 to 50 atms, at a WHSV ranging from 0.1 to 200 hours$^{-1}$ and with a molar ratio between aromatic and olefin ranging from 1 to 20.

3. The process according to claim 2, wherein the temperature is between 120 and 230° C., the pressure is between 20 and 45 atms, the WHSV is between 1 and 10 hours$^{-1}$ and the molar ratio between aromatic and olefin is between 2 and 8.

4. The process according to any one of claims 1 to 3, which comprises putting the aromatic hydrocarbon in contact with an olefin under at least partially liquid phase conditions.

5. The process according to claim 4, which comprises putting the aromatic hydrocarbon in contact with an olefin under substantially liquid phase conditions.

6. The process according to claim 1, wherein the cationic sites in the ERS-10 zeolite are prevalently occupied by hydrogen ions.

7. The process according to claim 6, wherein at least 80% of the cationic sites is occupied by hydrogen ions.

8. The process according to claim 1, wherein the ERS-10 zeolite comprises aluminum and silicon oxides.

9. The process according to claim 1, wherein the ERS-10 zeolite is combined with an inorganic oxide as ligand.

10. The process according to claim 9, wherein the inorganic oxide is alumina.

11. The process according to claim 9, wherein the ERS-10 zeolite is in a quantity ranging from 20 to 80% by weight of the catalyst.

12. The process according to claim 1, wherein the aromatic hydrocarbon is selected from the group consisting of benzene, toluene, xylene and their mixtures.

13. The process according to claim 12, wherein the aromatic hydrocarbon is benzene.

14. The process according to claim 1, wherein the olefin is selected from the group consisting of ethylene and propylene.

15. The process according to claim 1, wherein the olefin is added in at least two steps.

16. The process according to claim 1, wherein two or more catalytic beds or reactors in series are used.

17. A process for transalkylation of aromatic hydrocarbons which comprises putting an aromatic hydrocarbon in contact with a polyalkylated aromatic hydrocarbon in the presence of a catalyst containing ERS-10 zeolite.

18. The process according to claim 17 carried out at a temperature ranging from 100 to 350° C., at a pressure ranging from 10 to 50 atms, at a WHSV ranging from 0.1 to 200 hours$^{-1}$ and with a molar ratio between the aromatic hydrocarbon and the polyalkylated aromatic hydrocarbon ranging from 1 to 30.

19. The process according to claim 18, wherein the temperature is between 150 and 300° C., the pressure is between 20 and 45 atms, the WHSV is between 1 and 10 hours$^{-1}$ and the molar ratio between the aromatic hydrocarbon and the polyalkylated aromatic hydrocarbon is between 1 and 10.

20. The process according to any one of claims 17 to 19, which comprises putting the aromatic hydrocarbon in contact with the polyalkylated aromatic hydrocarbon under at least partially liquid phase conditions.

21. The process according to claim 17, wherein the aromatic hydrocarbon is selected from the group consisting of benzene, toluene, xylene and their mixtures.

22. The process according to claim 21, wherein the aromatic hydrocarbon is benzene.

23. The process according to claim 17, wherein the polyalkylated aromatic hydrocarbon is selected from the group consisting of diethylbenzene and diisopropylbenzene.

24. The process according to claim 17, wherein the ERS-10 zeolite comprises aluminum and silicon oxides.

25. The process according to claim 17, wherein the ERS-10 zeolite is combined with an inorganic oxide as ligand.

26. The process according to claim 25, wherein the ERS-10 zeolite is in a quantity ranging from 20 to 80% by weight of the catalyst.

27. The process according to claim 17, wherein the cationic sites in the ERS-10 zeolite are prevalently occupied by hydrogen ions.

28. The process according to claim 27, wherein at least 80% of the cationic sites is occupied by hydrogen ions.

29. A process for preparation of monoalkylated aromatic hydrocarbons which comprises:

1) putting an aromatic hydrocarbon in contact with a $C_2$–$C_4$ olefin, under alkylation conditions, in the presence of a catalyst comprising ERS-10 zeolite, 2) separating the product obtained from step (1) into (a) a fraction containing the aromatic hydrocarbon, (b) a fraction containing a monoalkylated aromatic hydrocarbon and (c) a fraction containing polyalkylated aromatic hydrocarbons, 3) putting the fraction containing polyalkylated aromatic hydrocarbons in contact with an aromatic hydrocarbon, under transalkylation conditions, in the presence of a catalyst comprising ERS-10 zeolite.

30. The process according to claim 29, wherein step (1) is carried out at a temperature ranging from 100 to 300° C., at a pressure ranging from 10 to 50 atms, at a WHSV ranging from 0.1 to 200 hours$^{-1}$ and with a molar ratio between aromatic and olefin ranging from 1 to 20, and step (3) is carried out at a temperature ranging from 100 to 350° C., at a pressure ranging from 10 to 50 atms, at a WHSV ranging from 0.1 to 200 hours$^{-1}$ and with a molar ratio between the aromatic hydrocarbon and the polyalkylated aromatic hydrocarbon ranging from 1 to 30.

31. The process according to claim 30, wherein in step (1) the temperature is between 120 and 230° C., the pressure is between 20 and 45 atms, the WHSV is between 1 and 10 hours$^{-1}$ and the molar ratio between said aromatic and said olefin is between 2 and 8, and in step (3) the temperature is between 150 and 300° C., the pressure is between 20 and 45 atms, the WHSV is between 1 and 10 hours$^{-1}$ and the molar ratio between the aromatic hydrocarbon and the polyalkylated aromatic hydrocarbon is between 1 and 10.

32. The process according to any one of claims 29 to 31 wherein in step (1) further comprises putting the aromatic hydrocarbon in contact with the olefin under at least partially liquid phase conditions.

33. The process according to claim 29, wherein at least 80% of the cationic sites of the ERS-10 zeolite is occupied by hydrogen ions.

34. The process according to claim 29, wherein the ERS-10 zeolite comprises aluminum and silicon oxides.

35. The process according to claim 29 wherein the aromatic hydrocarbon is benzene.

36. The process according to claim 29, wherein the olefin is selected from the group consisting of ethylene and propylene.

37. The process according to claim 29, wherein the polyalkylated aromatic hydrocarbon is diethylbenzene or diisopropylbenzene.

* * * * *

UNITED STATES PATENT AND TRADEMARK OFFICE
CERTIFICATE OF CORRECTION

PATENT NO. : 6,005,152

DATED : December 21, 1999

INVENTOR(S): Stefano AMARILLI et al.

It is certified that an error appears in the above-identified patent and that said Letters Patent is hereby corrected as shown below:

On the title page, item [73], the 2nd Assignee's name is misspelled. It should read as follows:

--[73] Assignees: Enichem S.p.A.; EniTecnologie S.p.A., both of San Donato Milanese, Italy--

Column 10, line 35, "The process according to any one of claims 29 to 31 wherein in step (1) further comprises putting the aromatic hydrocarbon in contact with the olefin under at least partially liquid phase conditions." should read --The process according to Claim 29 wherein step (1) comprises putting the aromatic hydrocarbon in contact with the olefin under at least partially liquid phase conditions.--.

Signed and Sealed this

Twenty-seventh Day of March, 2001

*Attest:*

NICHOLAS P. GODICI

*Attesting Officer*   *Acting Director of the United States Patent and Trademark Office*